United States Patent [19]
Brockamp et al.

[11] Patent Number: 5,162,221
[45] Date of Patent: Nov. 10, 1992

[54] FRUCTOSE-1,6-BISPHOSPHATE ALDOLASE, A PROCESS FOR THE PREPARATION THEREOF AND ITS USE

[75] Inventors: Hans-Peter Brockamp; Maria-Regina Kula, both of Niederzier; Friedrich Goetz, Tuebingen, all of Fed. Rep. of Germany

[73] Assignee: Forschungszentrum Juelich GmbH, Juelich, Fed. Rep. of Germany

[21] Appl. No.: 624,234

[22] Filed: Dec. 7, 1990

[30] Foreign Application Priority Data

Dec. 7, 1989 [DE] Fed. Rep. of Germany ....... 3940431
Aug. 21, 1990 [DE] Fed. Rep. of Germany ....... 4026382

[51] Int. Cl.$^5$ .......................... C12N 9/88; C12N 1/20; C12P 19/00; C12P 19/26
[52] U.S. Cl. ....................................... 435/232; 435/72; 435/183; 435/882
[58] Field of Search ................... 435/72, 232, 183, 882

[56] References Cited

U.S. PATENT DOCUMENTS

| | | | |
|---|---|---|---|
| 4,350,767 | 9/1982 | Zimmermann et al. | 435/183 |
| 4,605,622 | 8/1986 | Hasegawa et al. | 435/182 |
| 4,958,212 | 9/1990 | Stancesco et al. | 514/44 |
| 4,966,856 | 10/1990 | Ito et al. | 435/170 |

OTHER PUBLICATIONS

Serianni et al., "Enzymic Synthesis of C-Enriched Aldoses, Ketoses, and Their Phosphate Esters", Methods in Enzymology, vol. 89, pp. 83-92.
Gotz et al., "Purification and Characterisation of an Unusually Heat-Stable and Acid/Base-Stable Class I Fructose-1,6-bisphosphate Aldolase from *Staphylococcus aureus*", Eur. J. Biochem., 108, 1980, pp. 295-301.
Schleifer et al., "Description of a New Species of the Genus Staphylococcus; *Staphylococcus carnosus*", International Journal of Systematic Bacteriology, Apr. 1982, vol. 32, No. 2, pp. 153-156.

*Primary Examiner*—Herbert J. Lilling
*Attorney, Agent, or Firm*—Foley & Lardner

[57] ABSTRACT

A fructose-1,6-bisphosphate aldolase with obtained from *Staphylococcus carnosus* is disclosed. The aldolase has considerably improved stability as compared to aldolase from rabbit muscle, having an inactivation rate of 0.77%/d at 25° C. as compared with 59.3%/d for rabbit muscle aldolase. The aldolase is obtained by culturing *Staphylococcus carnosus* cells, mechanically disrupting the cell mass, and then working up the product by fractional ammonium sulfate precipitation, pH fractionation and ion exchange chromatography to provide F-1,6-BP aldolase with a specific activity of 25 U/mg in 21% yield. Particularly high yields are obtained by the aqueous 2-phase extraction and obtaining the enzyme from the upper phase by anion exchange chromatography. The aldolase is suitable for synthesis of carbohydrates and derivatives thereof by enzymatic reaction of aldehydes with DHAP.

3 Claims, 4 Drawing Sheets

FRUCTOSE-1,6-BISPHOSPHATE ALDOLASE, A PROCESS FOR THE PREPARATION THEREOF AND ITS USE

BACKGROUND OF THE INVENTION

The invention relates to a fructose-1,6-bisphosphate aldolase (F-1,6-BP aldolase), and a process for the preparation thereof and its use.

The current interest in specific aldol reactions and in the synthesis of monosaccharides which do not occur in nature and are difficult to obtain chemically has led to more and more attention being paid to the aldolases. The use of biocatalysts offers an efficient alternative for the organic synthesis of these biologically important substances, which may also be of use in medicine. The F-1,6-BP aldolase of rabbit muscle is today the only enzyme used in synthesis (A. E. Seriani et al., *Meth. Enzymol.*, 69: 83–92 (1982)). This aldolase isolated from rabbit muscle is costly and relatively unstable. On the other hand, a class 1 F-1,6-BP aldolase has already been isolated from *Staphylococcus aureus* and has similar enzymological properties to the aldolase isolated from rabbit muscle, but is considerably more stable to heat (F. Götz et al., *Eur. J. Biochem.* 108: 293–301 (1980)). However, the suitability of *Staphylococcus aureus* as an enzyme producer appears to be low because of its pathogenic properties.

SUMMARY OF THE INVENTION

It is therefore an object of the present invention to provide an aldolase which is more readily obtainable than the hitherto known F-1,6-BP aldolases from rabbit muscle or *Staphylococcus aureus* and which has a stability satisfactory for enzyme-catalyzed processes.

These and other objects are provided by a composition consisting essentially of fructose-1,6-bisphosphate aldolase (F-1,6-BP aldolase) isolated from *Staphylococcus carnosus*. In this regard, "consisting essentially of" defines a composition primarily containing the F-1,6-BP aldolase, and does not encompass the minute amounts of the enzyme naturally present in an organism in combination with other cellular components. More particularly, a composition consisting essentially of F-1,6-BP aldolase can be used to synthesize and accumulate carbohydrates on a commercial scale, and does not contain further enzymes that degrade the desired product.

A process for obtaining the F-1,6-BP aldolase is provided which comprises the steps of growing *Staphylococcus carnosus* cells in a culture liquid in a fermenter, removing the mass of *S. carnosus* cells from the culture liquid, disrupting the mass of cells to produce an enzyme-containing liquid, and obtaining F-1,6-BP aldolase from the enzyme-containing liquid. A process for carbohydrate synthesis, comprising the step of enzymatically reacting an aldehyde with dihydroxyacetone phosphate (DHAP) in the presence of the F-1,6-BP aldolase is also provided.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DESCRIPTION OF PREFERRED EMBODIMENTS

Figure 1:
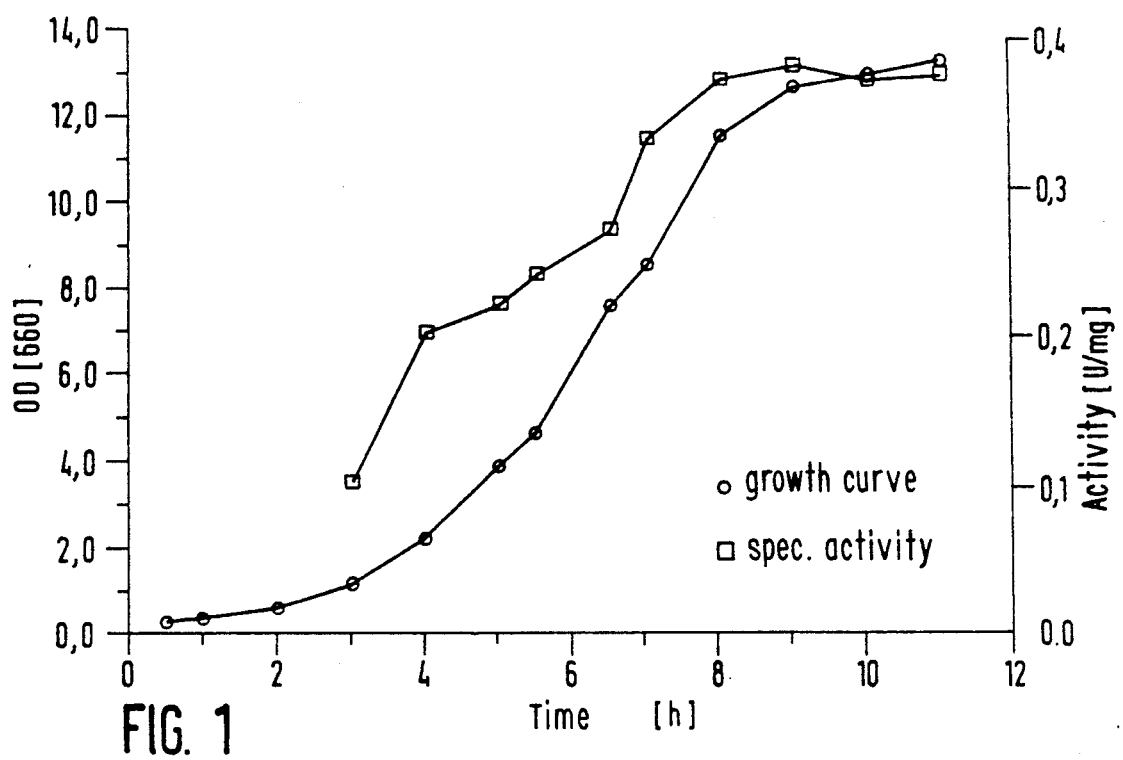
FIG. 1 shows plots of growth and enzyme production as a function of the culture time in the fermenter (5% pO$_2$).

The fructose-1,6-bisphosphate aldolase (F-1,6-BP aldolase) according to the invention is obtained from *Staphylococcus carnosus*.

This aldolase is considerably more stable than rabbit muscle aldolase, having an inactivation rate of 1%/d or less (e.g., found: 0.77%/d) under synthesis conditions at T=25° C.; pH 6.5; 20 mM DHAP; 75 mM glyoxylic acid; enzyme activity 2.9 U/ml or 25 U/mg, and having a stability in purified form ($\approx$25 U/mg) at 60° C. and 100° C. and at pH 7.5 in 0.06 M Tris-HCl buffer solution in Eppendorf tubes corresponding to a residual activity between 70 and 80%, and 20 and 30%, respectively after 30 minutes, in particular 76% and 26% respectively. Thus its thermal stability is only a little less than the aldolase from *Staphylococcus aureus*, the latter showing no noticeable loss of activity after 90 min at 100° C. The aldolase according to the invention does not have the serious disadvantage of being derived from an opportunistic pathogen.

The aldolase has the following characteristics:

It is a class I aldolase (forms a protonated Schiff's base with dihydroxyacetone phosphate, DHAP; activity toward F-1,6-BP not impaired by EDTA; completely inhibited by DHAP and NaBH$_4$);

It has K$_m$ values of 0.022 mM and 18.8 mM, respectively, for cleavage of F-1,6-BP to DHAP and glyceraldehyde 3-phosphate and of F-1-P to DHAP and glyceraldehyde at 37° C. and pH 7.5;

It has a specific activity (purified) of $\approx$25 U/mg of protein (protein determined by the Bradford method); a molecular weight of $\approx$33,000 daltons (no dissociation into subunits);

It has a pH optimum over the range from pH 6.5 to pH 9;

It retains 100% of its activity after 10 minutes at pH 1–12 (25° C.) and after 72 hours at pH 2 (4° C.);

It retains 70% of its activity after 5 minutes at 100° C. (pH 7.5) and after 90 minutes at 60° C. (pH 7.5);

It retains 100% of its activity after the purified lyophilisate has been stored for five days at:
a) room temperature
b) −20° C.;

It displays particularly good conversion of short-chain aliphatic aldehydes with additional increase in the conversion rate in the case of molecules with functional groups with a -I effect, i.e., negative inductive effect (electron withdrawing substituents).

The *Staphylococcus carnosus* used as enzyme producer can be obtained from natural sources without difficulty, in particular from dry uncooked sausage (see K. H. Schleifer et al., *Internat. J. System. Bacterial.*, 32: 153-156 (1982)) and is commercially available in the form of starter cultures. The *Staphylococcus carnosus* strain deposited under the number DSM 20 501 at the Deutsche Sammlung fur Mikroorganismen in Gottingen is particularly suited for use within the scope of the present invention.

The strain is grown in shake cultures in 500 ml Erlenmayer flasks containing 200 ml of medium at 110 rpm or a fermenter with a working volume between 5 and 10 l. An example of a suitable culture medium M 1) is one having the following composition:
1.0% tryptone
0.5% yeast extract
0.5% NaCl
0.1% Na$_2$HPO$_4$
1.0% glucose
pH 7.2
The pH was corrected using 3M NaOH and 3M H$_3$PO$_4$. Unless stated otherwise, the following parameters were maintained during the fermentation:

| Speed of rotation | 100 rpm |
|---|---|
| Temperature | 37° C. |
| Aeration | 5% pO$_2$ |
| Nutrient solution | M1 |
| pH | 7.2 |
| Culture time | 8-13 h |

The cells were harvested at the end of the logarithmic phase by centrifugation at 8,000 rpm for 10 minutes. The cells were disrupted by wet milling with glass beads.

The wet weight of the biomass from a fermentation volume of 9 l was 121 g. The purification steps indicated hereinafter were carried out at between 1° and 6° C. and 0.06M Tris-HCl buffer at pH 7.5. The enzyme was purified by fractional ammonium sulfate precipitation, pH fractionation and ion exchange chromatography.

Fractional ammonium sulfate precipitation

A cell-free crude extract (195 ml) was mixed with solid ammonium sulfate until the solution was 40% saturated. The pH was adjusted to 7.5 with 3M ammonia, and the precipitation was carried out for two hours in an ice bath. The precipitated constituents were removed by centrifugation at 20,000 rpm for 20 minutes. The (NH$_4$)$_2$SO$_4$ concentration was then increased stepwise to 60% and 80% saturation, again precipitated within the ice bath and centrifuged. To precipitate the aldolase, the supernatant was brought to 100% (NH$_4$)$_2$SO$_4$ saturation, and the pH was lowered to 5.0 with 7M acetic acid. The precipitate was resuspended in 50 ml of disruption buffer (0.06M Tris-HCl pH 7.5 containing 6 mM 2-mercaptoethanol).

pH fractionation

The pH of 50 ml of the 100% (NH$_4$)$_2$SO$_4$ fraction was lowered, while stirring vigorously, initially to 4.0 by dropwise addition of 7M acetic acid and then with 6M HCl to 3.6 and finally to 3.0. The precipitate which formed was in each case removed by centrifugation at 20,000 rpm for 20 min. The aldolase was located in the supernatant, which was desalted by diafiltration using an Amicon YM 10 ultrafiltration membrane.

Ion exchange chromatography

The desalted enzyme solution (30 ml) was loaded onto an 180 ml DEAE-Sephadex A 25 column which had previously been washed with 0.06M Tris-HCl buffer of pH 7.5 containing 0.1M NaCl. The enzyme was eluted by a linear salt gradient from 0.1 to 0.5M NaCl in 0.06M Tris-HCl buffer pH 7.5. The flow rate was 30 ml/h. The active fractions were combined and freeze-dried.

FIG. 1 shows plots of growth and enzyme production as a function of the culture time in the fermenter (5% pO$_2$). Table 1 which follows summarizes the purification results.

TABLE 1

| | Specific activity [U/mg]* | Purification factor | Yield % |
|---|---|---|---|
| Crude extract | 0.25 | 1 | 100 |
| (NH$_4$)$_2$SO$_4$ | 1.5 | 4.6 | 43 |
| pH fract. | 5.3 | 15.2 | 31 |
| DEAE chrom. | 25.0 | 71.4 | 21 |

*Protein determined by Bradford method (Anal. Biochem. Vol. 72 (1976) 248-254)

As an alternative, the aldolase can be separated, particularly expediently after cell harvesting and disruption, from biomass ballast by aqueous 2-phase extraction. In particular, polymer/salt mixtures and preferably polyethylene glycol/potassium phosphate mixtures may be used for this. Other salts, such as, for example, sulfate, can equally be used. Particularly expedient is a high content of PEG of low molecular weight, in particular a PEG with a molecular weight below about 1500 daltons.

The enzyme collects in the upper phase and can be back-extracted in another step; however, more industrially straightforward is direct use of the upper phase for subsequent separation on an anion exchanger column. Direct further processing in this way is possible without noticeable disadvantages.

Suitable column materials for this purpose are anion exchangers with aminoethyl, diethylaminoethyl (DEAE) and quarternary aminoethyl groups, which have normally been equilibrated to pH values of at least 5 and, in particular, to pH 7.5. DEAE-Sephadex ®, Mono Q and Q-Sepharose ® are preferred. Elution is carried out, in particular, with the salt content adjusted for a fractional flow through proteins, e.g., with a 0.25M salt solution with flow rates of 3-5 ml/min. The collected deposited fractions which contain the enzyme can be used as such or in freeze-dried form. An example of such a working up by aqueous 2-phase extraction follows.

Production of *S. carnosus* fructose-1,6-bisphosphate aldolase

I) Phase system
50% crude extract (40% w/w)
27% PEG 400
7% KP; (pH 7.5)
The upper phase contains 95%-99% of the enzyme activity with 0.8 U/mg of protein.

II) Q-Sepharose anion exchanger
A 50 ml column equilibrated with 20 mM Tris-HCl buffer pH 7.5, 0.15M NaCl, and 0.1% mercaptoethanol was used. The upper phase I was diluted 4:1 and loaded onto the exchanger.

Elution was performed with 20 mM Tris-HCl pH 7.5, 0.25M NaCl, and 0.1% mercaptoethanol. The yield was 80%-90%; 7.1 U/mg of protein.

III) Q-Sepharose anion exchanger

Equilibration as in II)

Positive fractions from run I were diluted 2:1 and loaded onto the exchanger. The protein was eluted with an NaCl gradient from 0.15 to 0.25M NaCl. The aldolase elutes at an NaCl concentration of 0.2M. The overall yield is 70%-80%; 13.1 U/mg of protein.

Enzyme characterization

Purified aldolase (40 μg/ml) was used for characterizing the enzyme, and 120 μg/ml were used for molecular weight determination.

Assignment to aldolase class I

The F-1,6-BP aldolase from *S. carnosus* can be assigned to the class I type of aldolases on the basis of the following characteristics.

The activity toward F-1,6-BP is unimpaired in the presence of various concentrations of EDTA.

*S. carnosus* aldolase is completely inhibited in the presence of DHAP and NaBH$_4$.

Singly- and doubly-charged cations have no effect on the aldolase activity.

In addition, *S. carnosus* aldolase is very specific for the natural substrate.

The molecular weight of the aldolase was determined by SDS-PAGE and found to be 33000 daltons (one subunit).

Michaelis-Menten K$_m$ values

Figure 2:
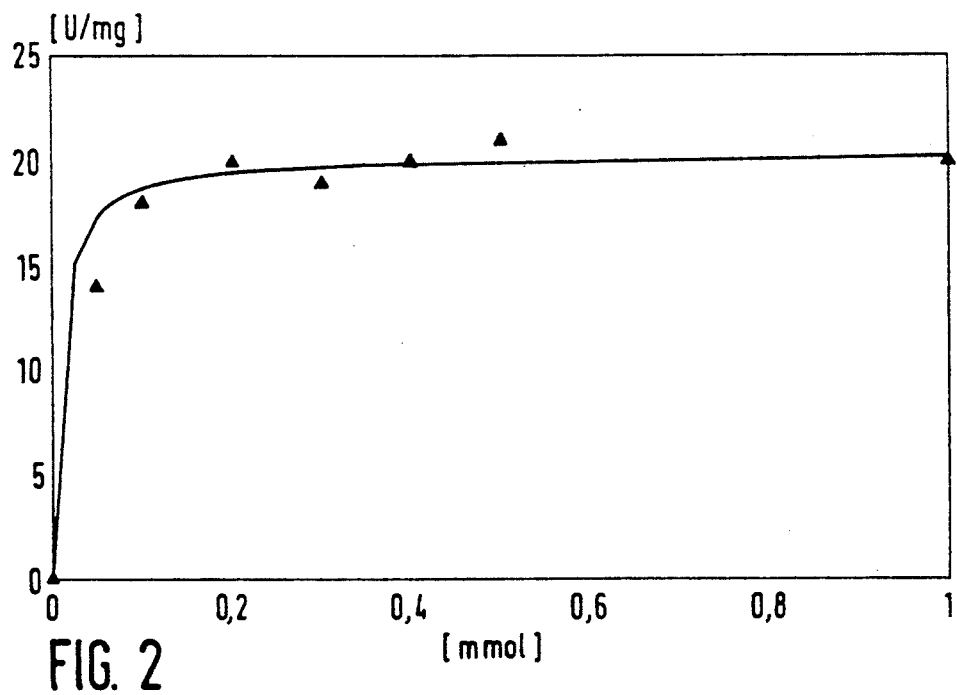
FIG. 2 shows the Michaelis-Menten plot for determining the K$_m$ of F-1,6-BP.
Figure 3:
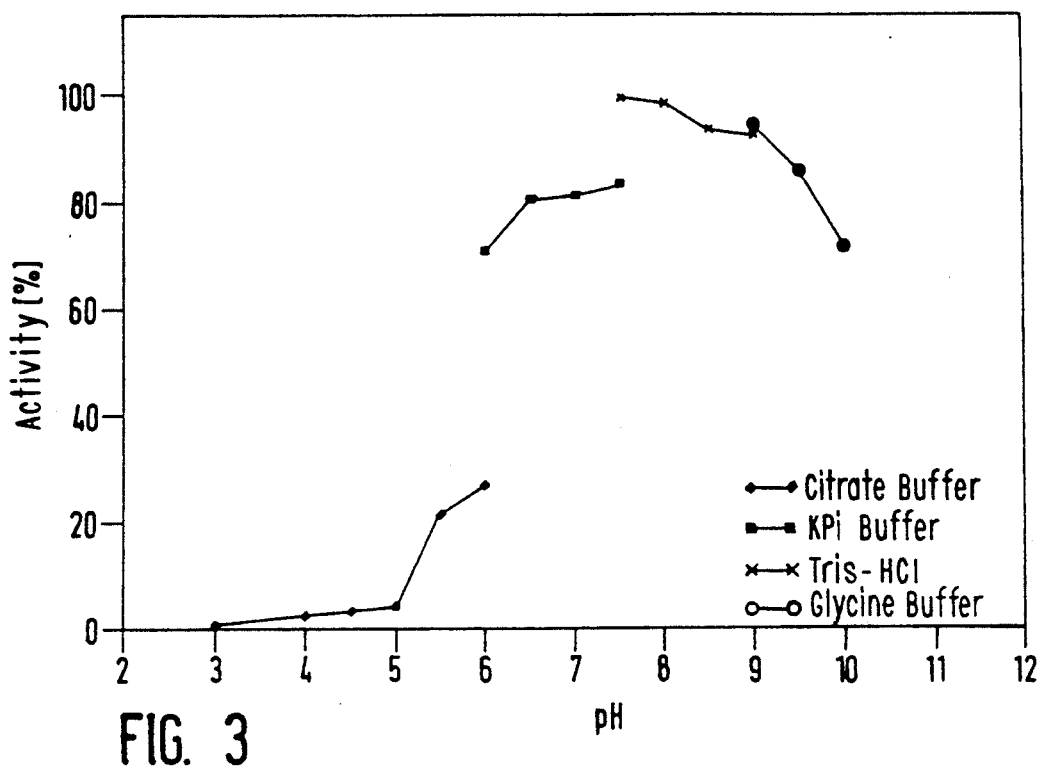
FIG. 3 is a plot of % activity versus pH, showing the pH optimum for aldolase according to the present invention.

The K$_m$ values for the substrates F-1,6-BP and F-1-P were determined from the enzyme activities of various substrate concentrations. FIG. 2 shows the Michaelis-Menten plot for determining the K$_m$ of F-1,6-BP.

K$_m$ for F-1,6-BP was 0.022 mM, and that for F-1-P was 18.8 mM, indicating that the aldolase is very specific for the natural substrate. The K$_m$ for F-1-P is a factor of 1000 greater than that for F-1,6-BP.

pH optimum

To determine the pH optimum, the enzyme activity of the aldolase was measured at 37° C. between pH 3 and pH 10 in the following buffers:

| | |
|---|---|
| 0.06 M citrate buffer | pH 3.0-6.0 |
| 0.06 M KP$_i$ buffer | pH 6.0-7.5 |
| 0.06 M Tris-HCl buffer | pH 7.5-9.0 |
| 0.06 M glycine buffer | pH 9.0-10.0 |

FIG. 3 shows that:

The pH optimum of the aldolase covers the pH range 6.5-9.0, with the peak being at pH 7.5.

The enzyme activities differ in the presence of the various buffers. Sodium citrate buffer shows the greatest inhibition of the enzyme.

Stability of the aldolase pH stability

Figure 4:
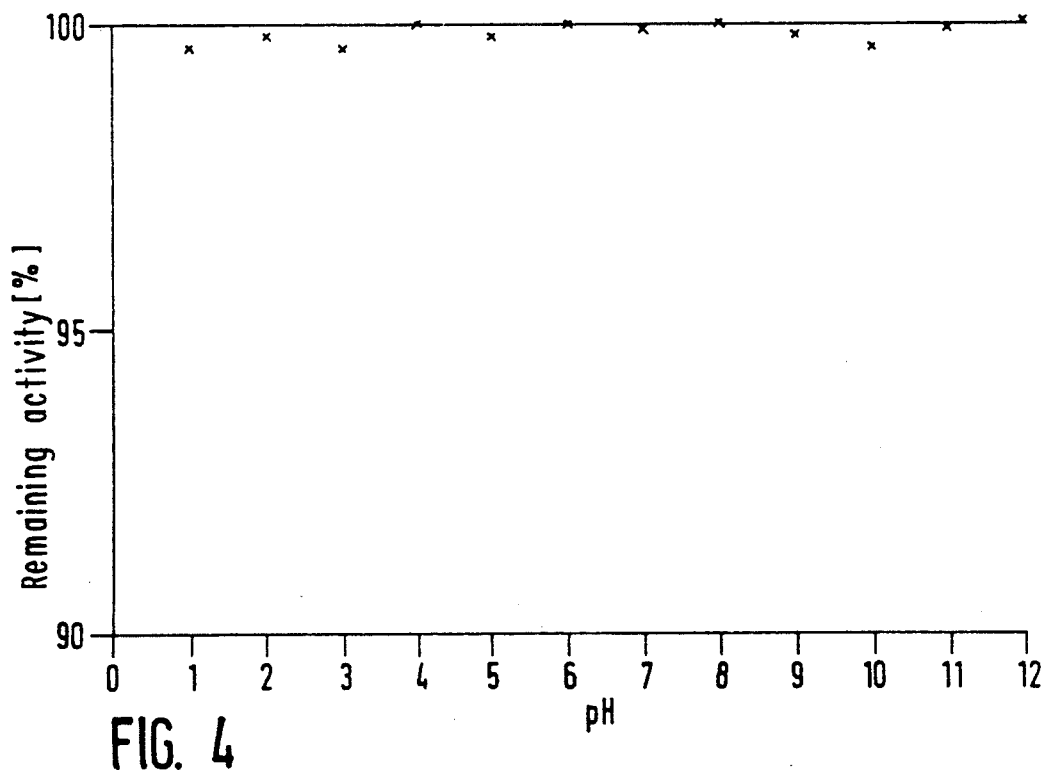
FIG. 4 shows the pH stability of aldolase according to the present invention after storage at room temperature between pH 1 and pH 12 for ten minutes.

The pH stability of the enzyme was determined by incubating the aldolase at room temperature (RT) between pH 1 and pH 12 for ten minutes. The results are shown in FIG. 4. Only 0.06M Tris-HCl buffer was used, the particular pH being adjusted with 2N NaOH or 2N HCl. After the incubation time, the sample solutions were readjusted to pH 7.5, and the enzyme activity was measured.

As FIG. 4 shows, *S. carnosus* aldolase has very good pH stability. It was established in another test that the aldolase activity was still 100% of the initial activity even after storage at pH 2 and 4° C. for 72 hours.

Thermal stability

Measurements were carried out to investigate the thermal stability of the aldolase.

1) The enzyme was incubated at temperatures between 40° C. and 100° C. in 0.06M Tris-HCl buffer of pH 7.5 for 5 minutes, and the dependence of the enzyme activity on the temperature was determined. Results are shown in FIG. 5.

2) In another series of tests, samples of the purified aldolase were incubated at 60° C. and 100° C. for various times to determine the dependence of the enzyme activity on time at two different temperatures. Results are shown in FIG. 6.

Figure 5:
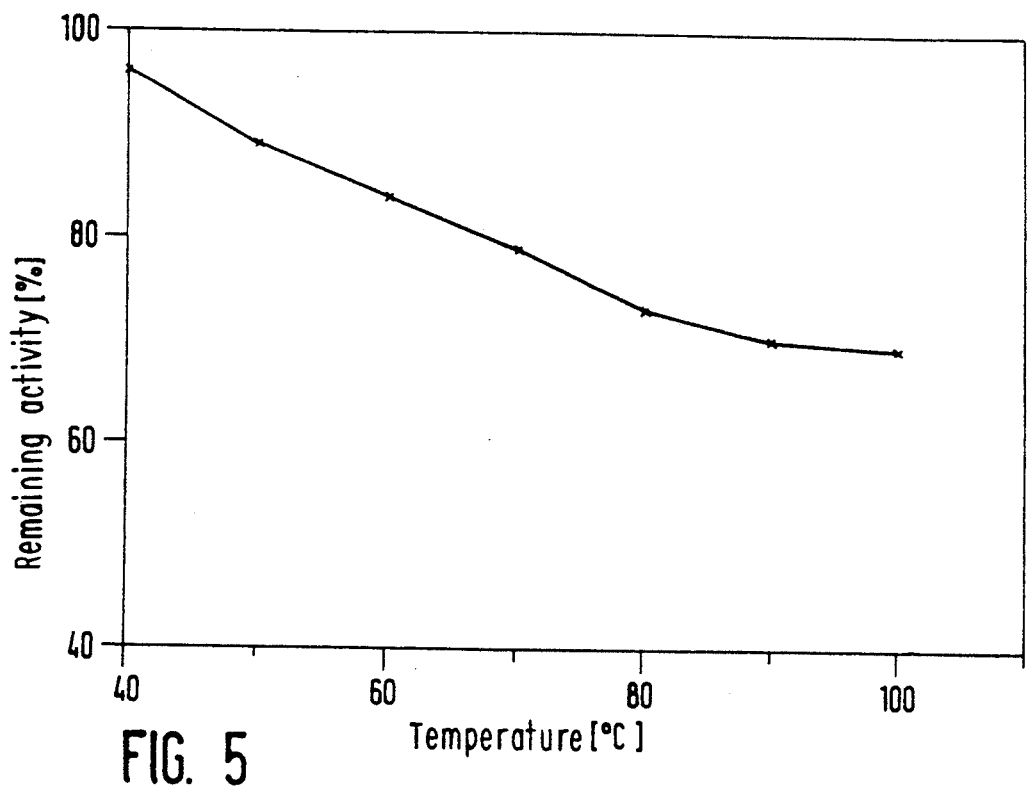
FIG. 5 shows the dependence of enzyme activity on temperature.
Figure 6:
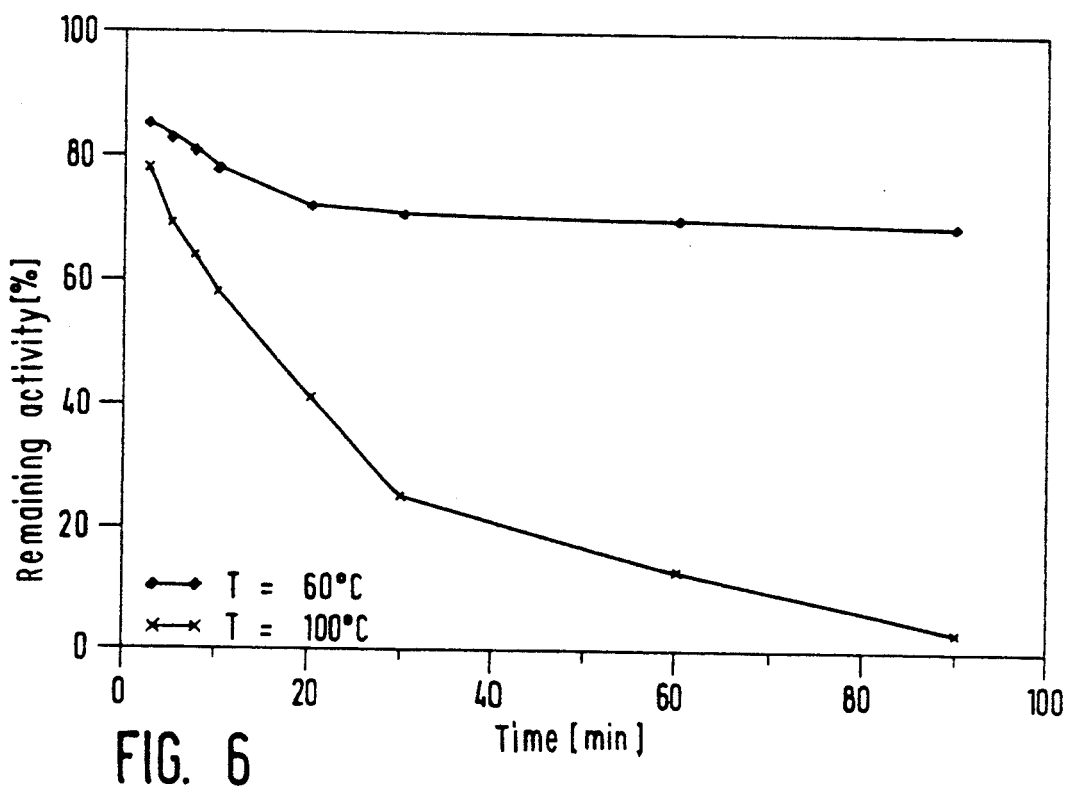
FIG. 6 demonstrates the relationship between enzyme activity and time at two different temperatures.

Both FIG. 5 and FIG. 6 show that the F-1,6-BP aldolase from *S. carnosus* is an enzyme with a relatively high thermal stability. Although its stability to heat is not like that described for the aldolase from *S. aureus*, which shows no loss of activity after 90 min at 100° C., the thermal stability is far better than that of rabbit muscle aldolase.

Storage stability of the aldolase

In order to gain information on storage stability, samples of the purified aldolase were mixed with various reagents and stored at room temperature (RT) or −20° C. for 5 days. The results are presented in Table 2, as percent activity remaining after storage.

TABLE 2

| | RT | −20° C. |
|---|---|---|
| 10% strength glycerol | 66% | 90% |
| 5% strength F-1, 6-BP | 98% | 100% |
| 4 mM mercaptoethanol | 54% | 91% |
| 5% strength albumin | 85% | 99% |
| Lyophilisate | 100% | 100% |

Stability comparison with rabbit muscle aldolase

The stability of the aldolase according to the invention was compared with that of rabbit muscle aldolase. The two enzymes were tested under the active conditions indicated in Table 3.

TABLE 3

| | Standard conditions | Active conditions |
|---|---|---|
| Temperature | 25° C. | 25° C. |
| pH | 6.5 | 6.0 |
| Solvent | Double-distilled H$_2$O | DHAP 20 mM Glyoxylic acid 75 mM in double-distilled H$_2$O |
| Enzyme conc. | 0.27 mg/ml | 0.27 mg/ml |

Figure 7:
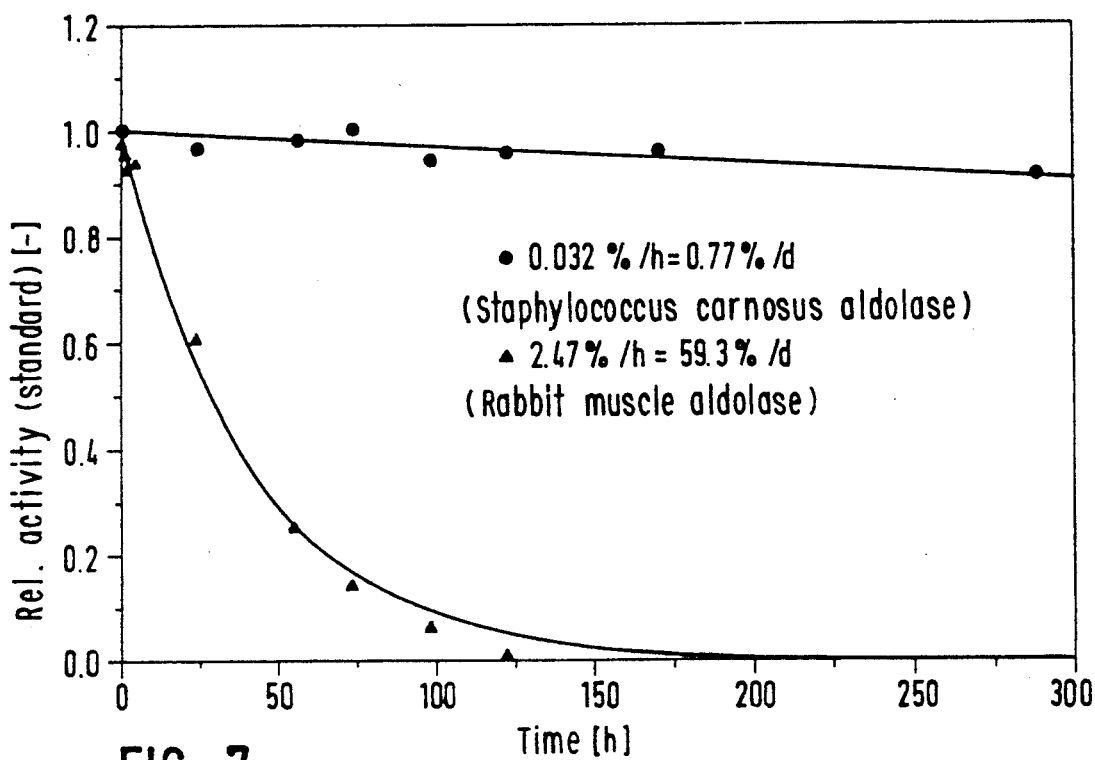
FIG. 7 shows the stability of aldolase from rabbit muscle and aldolase from *S. carnosus* over a period of 300 hours.

The enzyme concentration in the two tests was adjusted to be of comparable initial activity. It was 3.4 U/ml (9 U/mg) for rabbit muscle aldolase and 2.9 U/ml (25 U/mg) for *S. carnosus* aldolase. FIG. 7 shows the stability of the two aldolases over a period of 300 hours. To determine the inactivation rate, an exponential first-order inactivation was assumed, and the inactivation rate was derived from the exponential factor (1 = 100%/unit time).

Substrate spectrum

To determine the substrate spectrum, a number of aldehydes were tested by way of example. A mixture of 20 mM DHAP, 200 mM aldehyde, and 1–4 U/ml aldolase was used.

After incubation of the aldolase, TLC checks were carried out at intervals. In the mixtures containing the aldehydes indicated hereinafter, DHAP was no longer detectable after 5 to 8 hours.

| Aldolase substrates | |
| --- | --- |
| Aldehyde | $R_p$* of the product |
| Glyceraldehyde 3-phosphate | 0.36 |
| Methylglyoxal | 0.37 |
| D(+)-Glyceraldehyde | 0.44 |
| L(−)-Glyceraldehyde | 0.44 |
| D,L-Glyceraldehyde | 0.44 |
| Glycolaldehyde | 0.66 |
| Phthalaldehyde | 0.69 |
| Formaldehyde | 0.71 |
| Acetaldehyde | 0.93 |
| Chloroacetaldehyde | 1.08 |
| Propionaldehyde | 1.20 |
| 3-Methylmercaptopropionaldehyde | 1.24 |
| Isobutyraldehyde | 1.36 |
| Trimethylacetaldehyde | 1.41 |
| Butyraldehyde | 1.40 |
| 3-Ketobutyraldehyde | 1.48 |
| Isovaleraldehyde | 1.49 |
| Malonaldehyde | 1.49 |
| Pyridine-2-carbaldehyde | 1.50 |
| Pyridine-4-carbaldehyde | 1.50 |
| Phenylacetaldehyde | 1.53 |
| 2-Methylacetaldehyde | 1.54 |
| Valeraldehyde | 1.60 |

*$R_p$ value being analogous to $R_f$ value except for taking the (inorganic) phosphate front as the reference instead of the eluent front An example of a reaction catalyzed by F-1,6-BP aldolase is the synthesis of 5,6-dideoxyhexulose. Dihydroxyacetone phosphate (DHAP) was reacted on the preparative scale with propionaldehyde in the presence of F-1,6-BP aldolase at 25° C.

Mixture:
50 mM (5 mmol) DHAP
500 mM (50 mmol) propionaldehyde
40 U aldolase

The propionaldehyde was freshly distilled and stored under argon before the reaction. The progress of the reaction was observed both by polarimetry at a wavelength of 595 nm and by determining the remaining DHAP content. The reaction was complete after 6.5 hours, and the product was isolated as the cyclohexylammonium salt.

To elucidate the structure, 250 mg of the substance were dephosphorylated with acid phosphatase. The free sugar was peracetylated with acetic anhydride in pyridine. The $^1$H- and $^{13}$C-NMR spectra were used to identify the isolated compound unambiguously as the expected product.

The aldolase according to the invention is extremely useful for synthesizing carbohydrates and carbohydrate derivatives, in particular it can be used for preparing 6-deoxyfructose 1-phosphate, a precursor of the flavoring Furaneol (Wong et al., *J. Org. Chem.*, 48: 3493–3497 (1983)). The aldolase also can be used to obtain higher sugars with six or more carbon atoms, in particular with $C_8$, $C_9$, etc. (see Bednarski et al., *Tetrahedron Lett.*, 27: 5807–5810 (1986)). Complicated amino-sugars such as 1-deoxymannojirimycin, 1-deoxynojirimicin and 1,4-dideoxy-1,4-imino-D-arabinitol, which are important as effective β-glucosidase inhibitors (Ziegler et al., *Angew. Chemie*, 100: 737–738 (1988)), are more readily obtainable using the aldolase according to the invention, and some of them are endowed with inhibitory activity on HIV viruses (see Fleet et al., *FEBS Letters*, 237: 128–132 (1988)). Use of the aldolase for preparing pheromones is also possible, (M. Schultz et al., in *Tetrahedron Letters*, Vol. 31, pages 867–8 (1990)).

What is claimed is:

1. A purified fructose-1,6-biphosphate aldolase isolated from *Staphylococcus carnosus*, having the following properties:
    a molecular weight for one subunit of 33000 daltons, as determined by SDS-PAGE;
    a pH optimum of 7.5 to 9.0 in 0.06M Tris-HCl buffer at 37° C.; and
    an activity of 70% of the initial activity after 5 minutes at 100° C. in 0.06M Tris-HCl buffer adjusted to pH 7.5.

2. A purified aldolase as claimed in claim 1, isolated from *Staphylococcus carnosus* DSM 20 501.

3. A purified aldolase as claimed in claim 1, having a loss of activity of about 0.032%/h at 25° C. and pH 6 in 20 mM DHAP and 75 mM glyoxylic acid.

* * * * *